United States Patent [19]

Leutwiler

[11] Patent Number: 4,775,691

[45] Date of Patent: Oct. 4, 1988

[54] 4H-BENZO[4,5]CYCLOHEPTA[1,2-B]THIOPHENE DERIVATIVES

[75] Inventor: Albert Leutwiler, Bösingen, Switzerland

[73] Assignee: Sandoz Ltd., Basel, Switzerland

[21] Appl. No.: 145,870

[22] Filed: Jan. 20, 1988

Related U.S. Application Data

[63] Continuation of Ser. No. 82,875, Aug. 6, 1987, abandoned, which is a continuation of Ser. No. 937,584, Dec. 3, 1986, abandoned.

[30] Foreign Application Priority Data

Dec. 9, 1985 [GB] United Kingdom ................ 8530245

[51] Int. Cl.[4] ..................... A61K 31/38; C07D 333/74
[52] U.S. Cl. ........................................ 514/443; 549/44
[58] Field of Search ........................... 514/443; 549/44

[56] References Cited

U.S. PATENT DOCUMENTS

| | | | |
|---|---|---|---|
| 4,137,323 | 1/1979 | Bastian | 514/443 |
| 4,183,943 | 1/1980 | Bastian | 514/443 |
| 4,487,778 | 12/1984 | Plummer | 514/443 |
| 4,496,580 | 1/1985 | Martin et al. | 514/443 |

FOREIGN PATENT DOCUMENTS

| | | | |
|---|---|---|---|
| 0138765 | 4/1985 | European Pat. Off. | |
| 1112601 | 5/1968 | United Kingdom | 514/443 |

*Primary Examiner*—Alan Siegel
*Attorney, Agent, or Firm*—Gerald D. Sharkin; Robert S. Honor; Thomas O. McGovern

[57] ABSTRACT

[2-Halo-10-oxy-4H-benzo[4,5]cyclohepta[1,2-b]thiophen-4-ylidene]acetic acids, for example of formula I

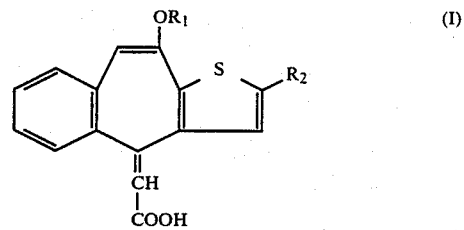

wherein $R_1$ is H or $C_{1-4}$alkyl and $R_2$ is halogen, their physiologically-hydrolysable and -acceptable esters, and salts thereof. Such compounds, esters and salts possess valuable pharmaceutical, in particular anti-inflammatory, antipyretic and analgesic, properties.

17 Claims, No Drawings

4H-BENZO[4,5]CYCLOHEPTA[1,2-B]THIOPHENE DERIVATIVES

This is a continuation of application Ser. No. 082,875, filed Aug. 6, 1987, now abandoned, which is a continuation of application Ser. No. 937,584, filed Dec. 3, 1986, now abandoned.

The present invention relates to novel 4H-benzo[4,5-]cyclohepta[1,2-b]thiophene derivatives as well as to processes for their production, their use as pharmaceuticals and pharmaceutical compositions comprising them.

European patent publications Nos. 0 035 903 and 0 115 690 and U.S. Pat. No. 4,376,124 relate to certain α-[5H-dibenzo[a,d]cyclohepten-5-ylidene]-carboxylic acids, disclosed as having anti-inflammatory as well as immunomodulatory activity. In Acta. Cryst. 37, 279–281 (1981) and Spanish Patent No. 497 898 the compound [9,10-dihydro-4H-benzocyclohepta[1,2-b]thiophen-4-ylidene]acetic acid is disclosed and described as an intermediate in the synthesis of tetracyclic compounds stated to possess CNS-activity. European Patent Publication No. 0 138 765 discloses certain α-[5H-dibenzo[a,d]cyclohepten-5-ylidene]-carboxylic acids having pharmaceutical, in particular, anti-inflammatory, antipyretic and analgesic properties.

In accordance with the present invention there is provided:

A [2-halo-10-oxy-4H-benzo[4,5]cyclohepta[1,2-b]thiophen-4-ylidene]acetic acid or a physiologically-hydrolysable and -acceptable ester or a salt thereof.

The said compounds, esters and salts, which are novel, have been found to possess particularly advantageous anti-pyretic as well as anti-inflammatory and analgesic activity as hereinafter described. More particularly they exhibit improved tolerability characteristics as compared with structurally related compounds, e.g. as disclosed in the aforementioned European Patent Publication No. 0 138 765.

It will be appreciated that the 4H-benzo[4,5]cyclohepta[1,2-b]thiophene nucleus in the compounds of the invention may bear substituents in addition to those specified at the 2-, 4- and 10-positions. Thus they may be further substituted, e.g. monosubstituted, in the benzene ring.

In a specific embodiment the present invention provides a compound of formula I

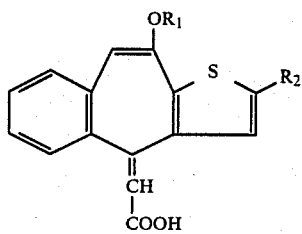

wherein
$R_1$ is hydrogen or $C_{1-4}$alkyl and
$R_2$ is halogen,
or a physiologically-hydrolysable and -acceptable ester or a salt thereof.

Alkyl moieties in the compounds of formula I may be branched or straight chain. By halogen is meant fluorine, chlorine, bromine or iodine.

Preferably $R_1$ is $C_{1-4}$alkyl, especially methyl. $R_2$ is preferably chlorine.

By the term "physiologically-hydrolysable and -acceptable ester" as applied to compounds of the invention, e.g. compounds of formula I, is meant esters in which the carboxylic group is esterified and which are hydrolysable under physiological conditions to yield an alcohol which is itself physiologically acceptable, e.g. non-toxic at desired dosage levels. Such esters include e.g. esters with aliphatic alcohols having 1 to 4 carbon atoms.

Salts of compounds of the invention. e.g. of compounds of formula I, include in particular their pharmaceutically acceptable salts. Such pharmaceutically acceptable salts include, e.g., alkali metal salts such as the sodium and potassium salts, as well as alkaline earth metal salts such as the calcium salts.

It will be appreciated that compounds of the invention wherein the 10-oxy group is 10-hydroxy, e.g. compounds for formula I, wherein $R_1$ is hydrogen, exist in both keto as well as in enol form, e.g. in the case of compounds of formula I, as tautomers of formula I'

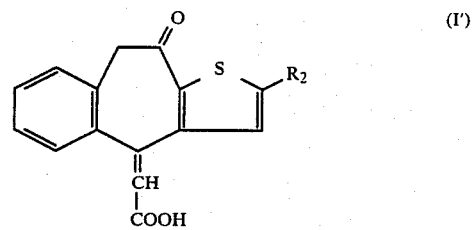

wherein $R_2$ is as defined above.

It is to be understood that where tautomeric forms occur the present invention embraces both keto and enol forms, i.e., although compounds of the invention are defined for convenience by reference to the enol form only, the invention is not to be understood as being in any way limited by the particular nomenclature or graphic representation employed. Similar considerations apply in relation to starting materials exhibiting keto/enol-tautomerism as hereinafter described.

The compounds of the invention, e.g. compounds of the formula I, exist in both cis and trans isomeric forms, i.e. as Z and E isomers. The present invention is to be understood as embracing both the individual cis and trans isomers as well as mixtures thereof. In the present specification and claims cis (Z) and trans (E) isomers are designated in accordance with conventional CIP-nomenclature [Angew. Chem. 94, 614 (1982) and Loc. cit.]. Thus the cis isomer is the isomer of formula I" and the trans isomer the isomer of formula I'''

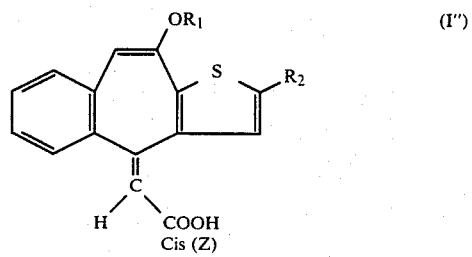

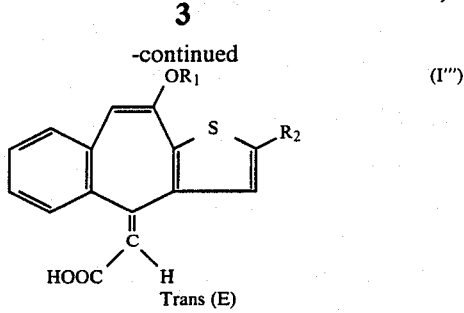

Trans (E)

In general the cis (Z) isomers are preferred. Accordingly the compounds of the invention are preferably in predominantly cis-form. Most preferably they are in pure or substantially pure cis-form.

Individual cis and trans isomers of compounds of the invention may be obtained in accordance with techniques known in the art, e.g. by separation of cis/trans isomer mixtures, for example as hereinafter described in example 2.

The present invention also provides a process for the production of compounds in accordance with the present invention as well as physiologically-hydrolysable and -acceptable esters and salts thereof, which process comprises:

(a) for the production of a physiologically-hydrolysable and -acceptable ester of a [2-halo-10-oxy-4H-benzo[4,5]cyclohepta[1,2-b]thiophen-4-ylidene]acetic acid, for example an ester of formula Ia

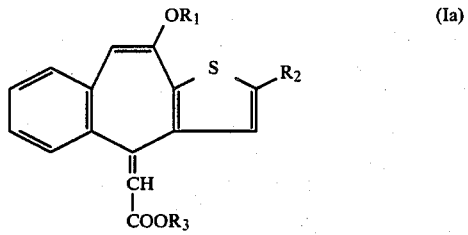

wherein $R_1$ and $R_2$ are as defined above and $R_3$ is $C_{1-4}$alkyl, reacting the corresponding 2-halo-10-oxy-4H-benzo[4,5]cyclohepta[1,2-b]thiophen-4-one, for example a compound of formula II

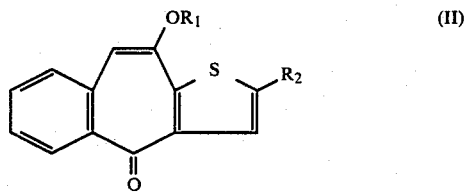

wherein $R_1$ and $R_2$ are as defined above, with an appropriate oxycarbonylmethylen-phosphonate, for example a compound of formula III

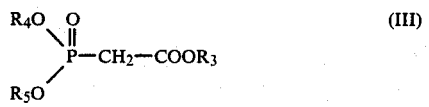

wherein $R_3$ is as defined above and $R_4$ and $R_5$ are each $C_{1-4}$alkyl or benzyl;

(b) for the production of a [2-halo-10-oxy-4H-benzo[4,5]cyclohepta[1,2-b]thiophen-4-ylidene]acetic acid, for example a compound of formula I as defined above, hydrolysing an ester thereof, for example hydrolysing an ester of formula Ia as defined above;

(c) for the production of a [2-halo-10-hydroxy-4H-benzo[4,5]cyclohepta[1,2-b]thiophen-4-ylidene]acetic acid or $C_{1-4}$alkyl ester thereof, for example a compound of formula I or Ia as defined above but wherein $R_1$ is specifically hydrogen, subjecting a corresponding [10-($C_{1-4}$alkoxy)-4H-benzo[4,5]cyclohepta[1,2-b]-thiophen-4-ylidene]acetic acid or $C_{1-4}$alkyl ester thereof, for example a compound of formula I or an ester of formula Ia as defined above but wherein $R_1$ is specifically $C_{1-4}$alkyl, to ether cleavage;

(d) converting a [2-halo-10-oxy-4H-benzo[4,5]cyclohepta[1,2-b]thiophen-4-ylidene]acetic acid, for example a compound of formula I as defined above, into a physiologically-hydrolysable and -acceptable ester thereof, for example into an ester of formula Ia as defined above;

and recovering a [2-halo-10-oxy-4H-benzo[4,5]cyclohepta[1,2-b]thiophen-4-ylidene]acetic acid, for example a compound of formula I as defined above, thus obtained in free form or in the form of a salt thereof.

Process step (a) above may be carried out in conventional manner, e.g. under Horner or like reaction conditions, for example by reaction of (II) with (III) in the presence of a base such as dry NaH with concomitant formation of the III-ylid. The reaction is suitably conducted in an inert solvent or diluent such as dimethyl sulfoxide at a temperature of from e.g. 50° to 120° C., under an inert atmosphere. As will be appreciated the oxycarbonyl moiety of the oxycarbonylmethylenphosphate starting material provides the ester moiety in the product compound. Appropriate oxycarbonylmethylenphosphonate starting materials are accordingly those wherein the said oxycarbonyl moiety represents a physiologically-hydrolysable and -acceptable ester residue in the product compound and wherein the oxy moiety is other than hydroxy. Conveniently the 10-oxy group in the starting material, e.g. in the case of compounds of formula II the group $R_1O$-, will be other than hydroxy in order to avoid possible unwanted reaction at this position. Suitably the 10-oxy group, e.g. $R_1O$- in formula II, is $C_{1-4}$alkoxy. Where such starting materials are employed and end-products are required having a 10-hydroxy group, these are suitably obtained e.g. by subsequent application of process step (c).

Process (b) may be carried out by any of the techniques known in the art for the hydrolysis of esters, for example by alkaline hydrolysis, e.g. in the presence of an alkali metal hydroxide at a temperature of from e.g. 20° C. to reflux in the presence of an inert solvent or diluent such as ethanol. $C_{1-4}$alkyl ester starting materials employed in process step (b) may be prepared in accordance with process step (a). Other esters suitable as starting materials may be prepared analogously.

Process step (c) may be carried out using any appropriate technique known in the art for the cleavage of enol-ether groups, for example by treatment with an appropriate organic or inorganic acid, e.g. a mineral acid such as $H_2SO_4$, HCl, HBr or phosphoric acid, or strong organic acids such as trifluoroacetic acid, as well as aliphatic and aromatic sulfonic acids. The reaction is suitably carried out e.g. in an inert organic solvent such as tetrahydrofuran at a temperature of from e.g. 20° C. to 70° C.

Conversion of initially obtained compounds, e.g. of formula I, to physiologically-hydrolysable and -acceptable esters in accordance with process step (d) may be carried out by conventional techniques, for example by reaction with an appropriate diazoalkane in an inert organic solvent, for example, ethylether at a temperature of from $-10°$ to $10°$ C. When the 10-oxy group in the starting material is other than hydroxy, e.g. when compounds of formula I wherein $R_1$ is $C_{1-4}$alkyl, are employed as starting materials, esterification may be accompanied by cleavage of this group so that, where end-products are required having the same 10-oxy group as the starting material, yields may be reduced. Cleavage at the 10-position may however be reduced by selection of appropriate esterification techniques, e.g. proceeding via the corresponding acid chloride as intermediate.

The starting materials of formula II for use in process step (a) may for example be prepared in accordance with the reaction sequence on the following page.

Reaction steps (e) and (f) can be carried out in accordance with conventional procedures, e.g. by: (e) reaction of IV with N-bromosuccinimide and; (f) reaction with a $C_{1-4}$alkanol, e.g. methanol, followed by treatment of the obtained product with an alkali metal hydroxide, e.g. KOH, for example in accordance with the general procedures hereinafter described in example 1, steps (ii) onwards. Starting materials of formula IV are known—see e.g. Helv. Chim. Acta. 49, 214 (1966)—or may be prepared analogously to the known compounds.

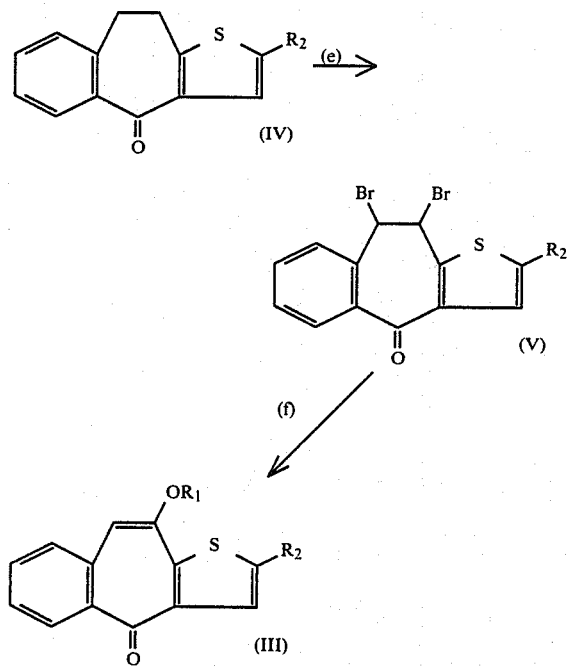

Where individual Z or E isomers of the compounds of the invention are required, separation of isomers is suitably performed employing the ester products of step (a) above. The individual Z and E ester isomers may then be hydrolysed, e.g. in accordance with process step (b).

The following examples are illustrative of the methods of the present invention.

EXAMPLE 1

(i) Preparation of [2-chloro-10-methoxy-4H-benzo[4,5]cyclohepta[1,2-b]thiophen-4-ylidene]acetic acid ethyl ester 4.7 g Phosphonoacetic acid-triethyl ester are combined, dropwise, with a suspension of 0.65 g sodium hydride (80% in white oil) in 25 ml dimethyl sulfoxide and the whole stirred for 15 mins. at room temperature. A solution of 3.2 g 2-chloro-10-methoxy-4H-benzo[4,5-]cyclohepta[1,2-b]thiophen-4-one in 120 ml dimethylformamide are then added, the reaction mixture stirred for 5 hours at 80° C. and then poured onto 1.7 liters $H_2O$. The aqueous mixture is extracted with ethyl acetate, the ethyl acetate phase washed 3x with $H_2O$ and 1x with brine and dried over $Na_2SO_4$. The title ester is obtained in the form of the (Z,E)-isomer mixture following evaporation of the solvent. Individual isomers are subsequently recovered in accordance with the procedures of example 2 below.

(ii) The starting material for the above process is prepared as follows:

(iia)
2-Chloro-9,10-dibromo-9,10-dihydro-4H-benzo-4,5]cyclohepta[1,2-b]thiophen-4-one 125 g 2-Chloro-4H-benzo[4,5]cyclohepta[1,2-b]thiophen-4-one, 179 g N-bromo-succinimide and 1 g dibenzoylperoxide in 1.7 liters $CCl_4$ are heated for 1.5 hours under reflux, stirred for 2 hours in an ice bath and filtered. The filtrate is evaporated and the residue stirred with 1.5 liters hexane and filtered off to yield the title compound: m.p.=130°–135° C.

(iib)
2-Chloro-10-methoxy-4H-benzo[4,5]cyclohepta[1,2-b]thiophen-4-one 50.8 g of the product of step (iia) are suspended in 1 liter $CH_3OH$ and heated under reflux for 13 hours. 21 g KOH are added and the mixture stirred for a further 7 hours under reflux. A precipitate forms on cooling and is filtered off, washed with $CH_3OH$ and then $H_2O$ and dried to yield the title compound: m.p.=190°–194° C.

EXAMPLE 2

[2-Chloro-10-methoxy-4H-benzo[4,5]cyclohepta[1,2-b[thiophen-4-ylidene]acetic acid ethyl ester-separation of (Z) and (E) isomers The isomer mixture obtained in accordance with example 1 is separated chromatographically employing silica gel 60 (Merck, 0.040–0.063 mm) and hexane:toluene (1:2) as eluant.

Rf values for the isomeric products (Merck DC plates, silica gel 60 $F_{254}$, coating thickness 0.25 mm with hexane: toluene (1:2) as eluant):
  (Z) isomer=0.24
  (E) isomer=0.15

EXAMPLE 3

[2-Chloro-10-methoxy-4H-benzo[4,5]cyclohepta[1,2-b]thiophene-4-ylidene]acetic acid 14 g of the product of example 1 [(Z)/(E)isomer mixture] or of example 2 [(Z) or (E) isomer individually] are dissolved in 140 ml ethanol, combined with 70 ml 2N NaOH and heated for 3 hours under reflux. The obtained solution is evaporated down to ⅓ volume and poured onto 250 ml ice water. The aqueous phase is adjusted to pH 1 by addition of 4N HCl and the obtained precipitate filtered off, washed with H$_2$O and dried to yield the title compound.

NMR data [(360 MHz) in CDCl$_3$] for the individual (Z) and (E) isomers:

| | |
|---|---|
| (Z) isomer = | H—C$_3$, s, δ = 6.93 |
| | H—C$_9$, s, δ = 6.16 |
| | O—CO—CH= s, δ = 5.89 |
| | (m.p. = 193–196° C. with decomposition) |
| (E) isomer = | H—C$_3$, s, δ = 6.98 |
| | H—C$_9$, s, δ = 6.23 |
| | O—CO—CH= s, δ = 5.92 |
| | (m.p. = 193–196° C. with decomposition) |

(δ ppm; s = singlet)

The following are prepared analogously to examples 1 through 3 above:

EXAMPLE 4

(analogous to example 1)

(i)

[2-Bromo-10-methoxy-4H-benzo[4,5]cyclohepta[1,2-b]thiophen-4-ylidene]acetic acid ethyl ester, (Z,E)-isomer mixture This is prepared via:

(iia)

2-Bromo-9,10-dibromo-9,10-dihydro-4H-benzo[4,5]cyclohepta[1,2-b]thiophen-4-one: m.p.=139°–147° C. with decomposition; and (iib)

2-Bromo-10-methoxy-4H-benzo[4,5]cyclohepta[1,2-b]thiophen-4-one: m.p.=178°–179° C.

EXAMPLE 5

(analogous to example 2)

[2-Bromo-10-methoxy-4H-benzo[4,5]cyclohepta[1,2-b]thiophen-4-ylidene]acetic acid ethyl ester Rf values for the isomeric products (Merck DC plates; silica gel 60 F$_{254}$, coating thickness 0.25 mm with CH$_2$Cl$_2$ as eluant)

(Z) isomer: Rf=0.45
(E) isomer: Rf=0.43

EXAMPLE 6

(analogous to example 3)

[2-Bromo-10-methoxy-4H-benzo[4,5]cyclohepta[1,2-b]thiophen-4-ylidene]acetic acid m.p. for the (Z) isomer=182°–191° C., with decomposition.

Compounds in accordance with the present invention, e.g. compounds of formula I and their physiologically-hydrolysable and -acceptable esters and pharmaceutically acceptable salts, (throughout the remainder of this text "active agents of the invention") exhibit pharmacological activity and are useful as pharmaceuticals.

In particular they exhibit anti-inflammatory activity, e.g. as indicated in (A) THE ADJUVANT ARTHRITIS TEST IN THE RAT. For this test, adjuvant arthritis is induced according to the method of Pearson and Wood, "Arthr. Rheum." 2, 440 (1959). Active agents of the invention are active in this test against established arthritis at dosages of from 5 to 30 mg/kg/day.

They also exhibit anti-pyretic activity, e.g. as indicated in (B) THE LPS (E. coli) INDUCED FEVER TEST IN THE RAT. For this test male rats (Sprague-Dawley) of 130–180 g are fasted overnight. Body temperature is measured the following morning using a rectal probe connected to a telethermometer. 1 ml/150 g body weight of heat killed suspension of E.coli (OD$_{600}$=1.555) in saline is then injected s.c.. Body temperature is measured 2 hours later and this value taken as the initial temperature. 6 hours after injection, the test animals receive an oral dosage of the test substance suspended in 0.5% tragacanth or tragacanth alone (control). Body temperature is again measured after a further 2 hours.

Increase in temperature for each rate is calculated and expressed as a % of average increase determined in the control group (ca. 1.5° to 2.0° C. above normal). The ED$_{50}$, estimated by regression analysis, is taken as the dosage at which increase in rectal temperature is 50% of that in the control group.

Active agents of the invention are active in this test at dosages of from 15 to 60 mg/kg.

They also exhibit analgesic activity, e.g. as indicated in (C) THE ARTHRITIS PAIN TEST IN THE RAT. For this test male rats (OFA) of 110–120 g are treated with 0.1 ml of a Myobacterium smegmatis suspension in paraffin oil (0.6 mg Mycobact./0.1 ml oil) injected i.c. into the tail root. Market arthritis in the hind-paws develops ca. 12 days after treatment. 30 mins. before administration of test-substance, control measurement is performed by flexing the foot joint of the right or left hind-paw using a Statham transducer until volcalisation occurs. Rats which do not vocalise are discarded. Test substance is administered orally and the flexion procedure repeated 1, 3 and 5 hours subsequently. The pressure at which vocalisation occurs is noted, the value recorded for each rat at each interval being the average value of three successive measurements. Animals in which the vocalisation threshold is doubled with respect to the control measurement are considered to be protected. The ED$_{50}$ estimated for each post-treatment time according to the Probit method is taken as the dosage at which 50% of animals are protected. Active agents of the invention are active in this test at dosages of from 3.2 to 100 mg/kg.

In view of their anti-inflammatory activity, active agents of the invention are useful in the treatment of inflammation, e.g. for the treatment of arthritis and rheumatic diseases such as polyarthritis chronica progrediens, as well as other chronic inflammatory conditions where anti-arthritic treatment is indicated.

In view of their anti-pyretic activity, active agents of the invention are useful as fever-controlling or reducing agents, e.g. for use in reduction of fever associated with infectious disease or in other conditions where supportive, anti-pyretic therapy is indicated.

In view of their analgesic activity, active agents of the invention are also useful as analgesic agents, in particular in the treatment of pain associated with inflammatory conditions.

Active agents of the invention may be administered by any conventional route, in particular enterally, especially orally in the form of e.g. tablets or capsules. They may also be administered parenterally, e.g. in the form of injectible solutions or suspensions.

For the above usages the required dosage will of course vary depending on the mode of administration, the particular condition to be treated the therapy desired and the particular active agent of the invention employed. In general however, satisfactory results are obtained on administration of active agents of the invention at a daily dosage of from about 5 to about 15 mg/kg animal body weight, p.o., for anti-inflammatory and analgesic effect and from about 6 to about 30 mg/kg animal body weight, p.o., for anti-pyretic effect. For larger mammals an indicated oral daily dosage is in the range of from about 350 mg to about 1.0 g, for anti-inflammatory and analgesic effect and from about 0.4 to about 2.0 g, for anti-pyretic effect, conveniently administered once, in divided doses 2 to 4 times a day, or in retard form. Dosage forms suitable for oral administration accordingly comprise from about 80 mg to about 1.0 g, (anti-inflammatory/analgesic) or from about 100 mg to about 2.0 g active agent of the invention, admixed with a solid or liquid pharmaceutical diluent or carrier therefor.

In connection with the above described uses, it is to be particularly noted that active agents of the invention have surprisingly been found to exhibit substantially reduced side effects, in particularly ulcerogenicity, as compared with other known non-steroidal anti-inflammatory agents. As already noted active agents of the invention also exhibit improved tolerability characteristics as compared with compounds disclosed in European Patent Publication No. 0 138 765.

As indicated above, a suitable daily dosage for any specific active agent in accordance with the invention will depend on its relative potency. For the preferred compound in accordance with the invention, [2-chloro-10-methoxy-4H-benzo[4,5]-cyclohepta[1,2-b]thiophen-4-ylidene]acetic acid (E)-isomer, (Compound A in the table below) results obtained in test A, B and C above compared with results for acetyl-salicylic acid (Compound B in the table below), are as follows:

| COMPOUND | ED$_{50}$ VALUES | | |
| --- | --- | --- | --- |
| | TEST A mg/kg/day | TEST B mg/kg | TEST C mg/kg |
| A | 10 ± 2 | 14 ± 5 | 18 |
| B | 240 | 161 | 90 |

Indicated daily dosages for compound A in accordance with the invention in relation to anti-inflammatory therapy will accordingly be of the order of 1/24 of those commonly employed using acetylsalicylic acid as medication. In relation to anti-pyretic and analgesic therapy, daily dosages for the compound A will be of the order of 1/10 and 1/5 respectively of those commonly employed using acetylsalicylic acid as medication.

In accordance with the foregoing the present invention further provides:

(i) an active agent of the invention for use as pharmaceutical, e.g. for use as an anti-inflammatory, antipyretic or analgesic agent;

(ii) a method of treating inflammation, or of controlling or reducing fever, or of alleviating pain in a subject in need of such treatment, which method comprises administering to said subject an anti-inflammatorily, antipyretically or analgesically effective amount of an active agent of the invention; as well as (iii) a pharmaceutical composition comprising an active agent of the invention, together with a pharmaceutically acceptable diluent or carrier therefor.

I claim:

1. A compound of formula I

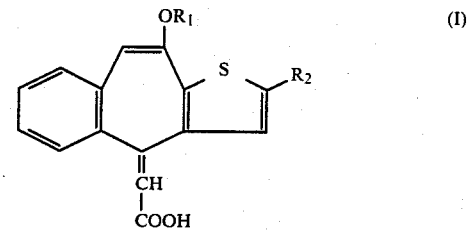

wherein
R$_1$ is hydrogen or C$_{1-4}$alkyl and
R$_2$ is halogen
or a physiologically-hydrolysable and -acceptable ester or a salt thereof.

2. [2-Chloro-10-methoxy-4H-benzo[4,5]cyclohepta[1,2-b]-thiophen-4-ylidene]acetic acid according to claim 1, or salt thereof.

3. A compound or ester according to claim 1 selected from the group consisting of: [2-Chloro-10-methoxy-4H-benzo[4,5]-cyclohepta[1,2-b]thiophen-4-ylidene]acetic acid ethyl ester [2-Bromo-10-methoxy-4H-benzo[4,5]cyclohepta[1,2-b]-thipophen-4-ylidene]acetic acid and [2-Bromo-10-methoxy-4H-benzo[4,5]cyclohepta[1,2-b]thiophen-4-ylidene]acetic acid ethyl ester.

4. A compound, ester or salt according to claim 1 in predominantly cis-isomeric form.

5. A compound or salt according to claim 2 in predominantly cis-isomeric form.

6. A compound, ester or salt according to claim 1 in pure or substantially pure cis-isomeric form.

7. A compound or salt according to claim 2 in pure or substantially pure cis-isomeric form.

8. A pharmaceutical composition comprising a [2-halo-10-oxy-4H-benzo[4,5]cyclohepta[1,2-b]thiophen-4-ylidene]acetic acid according to claim 1, or a physiologically-hydrolysable and -acceptable ester or a pharmaceutically acceptable salt thereof, together with a pharmaceutically acceptable diluent or carrier therefor.

9. A compound of formula I

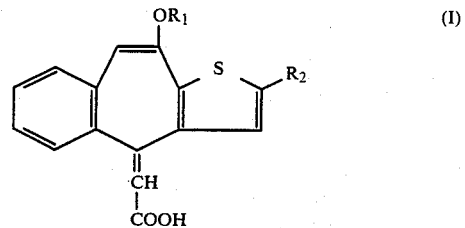

wherein
R$_1$ is C$_{1-4}$alkyl and
R$_2$ is halogen,
or a physiologically-hydrolysable and -acceptable ester or a pharmaceutically acceptable salt thereof.

10. A compound according to claim 9 in predominantly cis-isomeric form.

11. A compound according to claim 9 in pure or substantially pure cis-isomeric form.

12. A method of treating inflammation in a subject in need of such treatment which comprises administering an anti-inflammatory effective amount of a compound of claim 1 to said subject.

13. A method of controlling or reducing fever in a subject in need of such treatment, which comprises administering an antipyretical effective amount of a compound of claim 1 to said subject.

14. A method of alleviating pain in a subject in need of such treatment, which comprises administering an analgesically effective amount of a compound of claim 1 to said subject.

15. A method of treating inflammation in a subject in need of such treatment which comprises administering an anti-inflammatory effective amount of a compound of claim 9 to said subject.

16. A method of controlling or reducing fever in a subject in need of such treatment, which comprises administering an antipyretical effective amount of a compound of claim 9 to said subject.

17. A method of alleviating pain in a subject in need of such treatment, which comprises administering an analgesically effective amount of a compound of claim 9 to said subject.

* * * * *